United States Patent
Stopek et al.

(10) Patent No.: US 9,005,243 B2
(45) Date of Patent: *Apr. 14, 2015

(54) BUTTRESS AND SURGICAL STAPLING APPARATUS

(71) Applicant: Covidien LP, Mansfield, MA (US)

(72) Inventors: Megan Stopek, St. Louis Park, MN (US); Brian Nentwick, Greenfield Center, NY (US); Philippe Gravagna, Irigny (FR); Yves Bayon, Lyons (FR); Dagmar Dassonville, Charnoz (FR); Alfredo Meneghin, Laval (FR); Julie Lecuivre, Le Bois d'Oingt (FR)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/945,218

(22) Filed: Jul. 18, 2013

(65) Prior Publication Data

US 2013/0310873 A1 Nov. 21, 2013

Related U.S. Application Data

(60) Continuation of application No. 13/274,521, filed on Oct. 17, 2011, now Pat. No. 8,496,683, which is a division of application No. 11/823,340, filed on Jun. 27, 2007, now Pat. No. 8,062,330.

(51) Int. Cl.
| | | |
|---|---|---|
| *A61B 17/08* | (2006.01) | |
| *A61B 17/04* | (2006.01) | |
| *B29C 39/12* | (2006.01) | |
| *A61B 17/072* | (2006.01) | |
| *A61B 17/00* | (2006.01) | |

(52) U.S. Cl.
CPC ......... *B29C 39/123* (2013.01); *A61B 17/07207* (2013.01); *A61B 17/07292* (2013.01); *A61B 2017/00526* (2013.01); *A61B 2017/00849* (2013.01); *A61B 2017/00889* (2013.01); *A61B 2017/00893* (2013.01); *A61B 17/072* (2013.01)

(58) Field of Classification Search
USPC .......... 227/175.1, 176.1, 179.1, 180.1, 178.1, 227/19; 606/139–143, 215
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,825,007 A | 7/1974 | Rand |
| 4,347,847 A | 9/1982 | Usher |
| 4,354,628 A | 10/1982 | Green |

(Continued)

FOREIGN PATENT DOCUMENTS

| | | |
|---|---|---|
| CA | 2 667 434 | 5/2008 |
| DE | 19924311 A1 | 11/2000 |

(Continued)

OTHER PUBLICATIONS

International Search Report from application EP 06016962.0 dated Jan. 3, 2007.

(Continued)

*Primary Examiner* — Gregory Anderson
*Assistant Examiner* — Christina Lauer

(57) ABSTRACT

Multilayer structures including a porous layer and a non-porous layer are useful as buttresses when associated with a surgical stapling apparatus.

16 Claims, 5 Drawing Sheets

(56) References Cited

U.S. PATENT DOCUMENTS

| | | |
|---|---|---|
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,104,400 A | 4/1992 | Berguer et al. |
| 5,201,745 A | 4/1993 | Tayot et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 * | 12/2001 | Hamilton et al. ............. 606/151 |
| 6,330,965 B1 | 12/2001 | Milliman et al. |
| 6,436,030 B2 | 8/2002 | Rehil |
| 6,451,032 B1 | 9/2002 | Ory et al. |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,596,304 B1 | 7/2003 | Bayon et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,706,684 B1 | 3/2004 | Bayon et al. |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| RE39,172 E | 7/2006 | Bayon et al. |
| 7,128,748 B2 | 10/2006 | Mooradian et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 * | 11/2011 | Prommersberger et al. .. 606/215 |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,192,460 B2 | 6/2012 | Orban |
| 8,210,414 B2 | 7/2012 | Bettuchi |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,871 B2 | 4/2013 | Racenet |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,474,677 B2 | 7/2013 | Woodard, Jr. |
| 8,479,968 B2 | 7/2013 | Hodgkinson |
| 8,496,683 B2 * | 7/2013 | Prommersberger et al. .. 606/215 |
| 8,511,533 B2 | 8/2013 | Viola |

(56) References Cited

U.S. PATENT DOCUMENTS

| | | |
|---|---|---|
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,684,250 B2 | 4/2014 | Bettuchi |
| 8,757,466 B2 | 6/2014 | Olson |
| 8,789,737 B2 | 7/2014 | Hodgkinson |
| 8,820,606 B2 | 9/2014 | Hodgkinson |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2003/0023316 A1 | 1/2003 | Brown et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0105510 A1 | 6/2003 | DiMatteo et al. |
| 2003/0114866 A1 | 6/2003 | Ulmsten et al. |
| 2003/0120284 A1 | 6/2003 | Palacios et al. |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0132365 A1 | 7/2004 | Therin et al. |
| 2004/0138762 A1 | 7/2004 | Therin et al. |
| 2004/0142621 A1 | 7/2004 | Carroll et al. |
| 2004/0172048 A1 | 9/2004 | Browning |
| 2004/0175408 A1 * | 9/2004 | Chun et al. ............ 424/426 |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban, III et al. |
| 2006/0004407 A1 | 1/2006 | Hiles et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2008/0029570 A1 | 2/2008 | Shelton et al. |
| 2008/0082126 A1 | 4/2008 | Murray et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0187179 A1 | 7/2012 | Gleiman |
| 2012/0241499 A1 | 9/2012 | Baxter |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0277411 A1 | 10/2013 | Hodgkinson |
| 2013/0306707 A1 | 11/2013 | Viola |
| 2013/0327807 A1 | 12/2013 | Olson |
| 2014/0012317 A1 | 1/2014 | Orban |

(56) References Cited

U.S. PATENT DOCUMENTS

| | | | |
|---|---|---|---|
| 2014/0021242 | A1 | 1/2014 | Hodgkinson |
| 2014/0027490 | A1 | 1/2014 | Marczyk |
| 2014/0034704 | A1 | 2/2014 | Ingmanson |
| 2014/0048580 | A1 | 2/2014 | Merchant |
| 2014/0061280 | A1 | 3/2014 | Ingmanson |
| 2014/0061281 | A1 | 3/2014 | Hodgkinson |
| 2014/0084042 | A1 | 3/2014 | Stopek |
| 2014/0097224 | A1 | 4/2014 | Prior |
| 2014/0117066 | A1 | 5/2014 | Aranyi |
| 2014/0130330 | A1 | 5/2014 | Olson |
| 2014/0131418 | A1 | 5/2014 | Kostrzewski |
| 2014/0131419 | A1 | 5/2014 | Bettuchi |
| 2014/0138423 | A1 | 5/2014 | Whitfield |
| 2014/0151431 | A1 | 6/2014 | Hodgkinson |
| 2014/0155916 | A1 | 6/2014 | Hodgkinson |
| 2014/0158742 | A1 | 6/2014 | Stopek |
| 2014/0166721 | A1 | 6/2014 | Stevenson |
| 2014/0197224 | A1 | 7/2014 | Penna |
| 2014/0203061 | A1 | 7/2014 | Hodgkinson |
| 2014/0217147 | A1 | 8/2014 | Milliman |
| 2014/0217148 | A1 | 8/2014 | Penna |
| 2014/0239046 | A1 | 8/2014 | Milliman |
| 2014/0239047 | A1 | 8/2014 | Hodgkinson |

FOREIGN PATENT DOCUMENTS

| | | | |
|---|---|---|---|
| EP | 0594148 A1 | 4/1994 | |
| EP | 1 256 318 | 11/2002 | |
| EP | 1520525 A1 | 4/2005 | |
| EP | 1702570 A1 | 9/2006 | |
| EP | 1815804 A2 | 8/2007 | |
| EP | 2005895 A2 | 12/2008 | |
| EP | 2008595 A2 | 12/2008 | |
| EP | 2 090 252 | 8/2009 | |
| EP | 2198787 A1 | 6/2010 | |
| EP | 2 236 099 | 10/2010 | |
| EP | 2236098 A2 | 10/2010 | |
| EP | 2 436 348 | 4/2012 | |
| EP | 2 462 880 | 6/2012 | |
| EP | 2 517 637 | 10/2012 | |
| EP | 2 586 380 | 5/2013 | |
| EP | 2 604 195 | 6/2013 | |
| EP | 2 604 197 | 6/2013 | |
| EP | 2 620 106 | 7/2013 | |
| EP | 2 630 922 | 8/2013 | |
| EP | 2 644 125 | 10/2013 | |
| JP | 2000166933 A | 6/2000 | |
| JP | 07124166 | 5/2007 | |
| WO | 9005489 A1 | 5/1990 | |
| WO | 9607356 A1 | 3/1996 | |
| WO | 9817180 A1 | 4/1998 | |
| WO | 9945849 A1 | 9/1999 | |
| WO | 03082126 A1 | 10/2003 | |
| WO | 03105698 A2 | 12/2003 | |
| WO | 2005079675 A2 | 9/2005 | |
| WO | WO 2005/079675 | 9/2005 | |
| WO | 2006023578 A2 | 3/2006 | |
| WO | 2006044490 A2 | 4/2006 | |
| WO | 2006083748 A1 | 8/2006 | |
| WO | 2010075298 A2 | 7/2010 | |
| WO | 2011143183 A2 | 11/2011 | |
| WO | 2012044848 A1 | 4/2012 | |

OTHER PUBLICATIONS

International Search Report from application PCT/US05/36740 mailed Mar. 23, 2007.
International Search Report from Application No. PCT/US2008/002981 dated Jun. 26, 2008.
International Search Report from Application No. EP 08 25 1779 dated Jul. 23, 2008.
European Search Report for EP 08251990.1-2310 date of completion is Mar. 11, 2010 (5 pages).
International Search Report corresponding to European Application No. EP 12 15 2229.6, completed on Feb. 23, 2012 and mailed on Mar. 1, 2012; 4 pages.
International Search Report corresponding to European Application No. EP 12 15 0511.9, completed on Apr. 16, 2012 and mailed on Apr. 24, 2012; 7 pages.
International Search Report corresponding to European Application No. EP 12 15 2541.4, completed on Apr. 23, 2012 and mailed on May 3, 2012; 10 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
European Search Report for EP 12194784.0 date of completion is Jan. 22, 2013 (12 pages).
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).

* cited by examiner

BUTTRESS AND SURGICAL STAPLING APPARATUS

CROSS-REFERENCE TO RELATED APPLICATIONS

This application is a continuation of U.S. patent application Ser. No. 13/274,521, filed Oct. 17, 2011, which is a divisional of U.S. application Ser. No. 11/823,340 filed Jun. 27, 2007, now U.S. Pat. No. 8,062,330, the entire disclosures of each of the above-identified applications are hereby incorporated by reference herein.

BACKGROUND

1. Technical Field

The present disclosure relates to surgical buttresses which can be releasably attached to a surgical stapling apparatus. The buttresses contain a porous layer and a non-porous layer.

2. Background of Related Art

Surgical stapling devices have found widespread application in surgical operations where body tissue must be joined or removed. When operating on certain tissue, such as lung, esophageal, intestinal, duodenal, and vascular tissue, it is important to effectively seal the tissue which can be particularly prone to air or fluid leakage. Preventing or reducing air or fluid leakage can significantly decrease post operative recovery time. Thus, it would be advantageous to provide a material for use with a surgical stapling device which enhances sealing at the surgical wound site.

SUMMARY

Buttresses having a porous layer and a non-porous layer are described herein. The multilayer buttresses are suitable for use in connection with a surgical stapling apparatus and assist in the sealing of tissue to prevent the leakage of fluids and gases. The surgical stapling apparatus includes a staple cartridge having a surface with at least one opening through which a staple may be ejected. The surgical stapling apparatus further includes an anvil having a surface against which an ejected staple may be deformed. A buttress in accordance with the present disclosure may be associated with either the staple cartridge, the anvil, or both.

In embodiments, the porous layer possesses haemostatic properties. In embodiments, the non-porous layer has anti-adhesion properties.

DETAILED DESCRIPTION OF PREFERRED EMBODIMENTS

Figure 1:
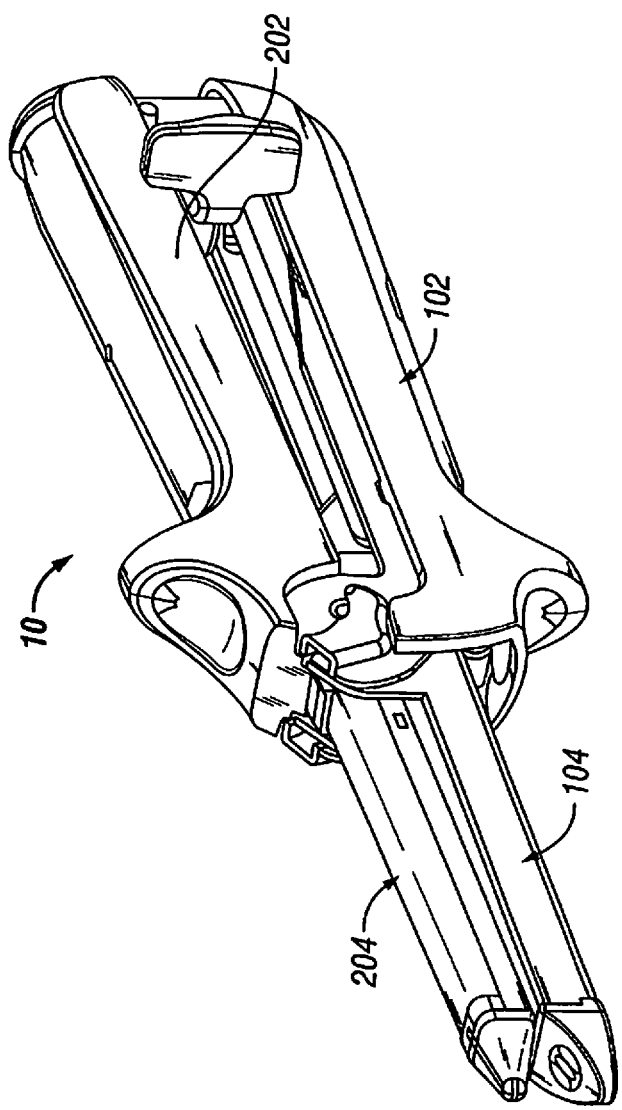
FIG. 1 is a perspective view of one illustrative embodiment of a linear surgical stapling apparatus.
Figure 2A:
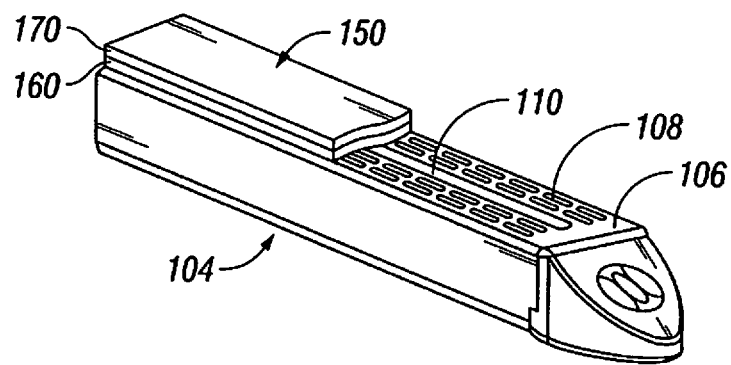
FIG. 2A is a perspective view of a staple cartridge that includes a multilayer buttress in accordance with the present disclosure.
Figure 2B:
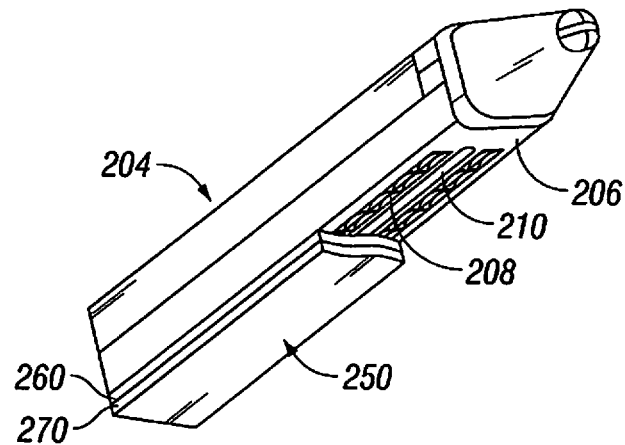
FIG. 2B is a perspective view of a staple anvil that includes a multilayer buttress in accordance with the present disclosure.

Embodiments of the presently disclosed multilayer buttress and surgical stapling apparatus will now be described in detail with reference to the drawing figures wherein like reference numerals identify similar or identical elements.

The multilayer surgical buttress described herein may be used in sealing a wound by approximating the edges of wound tissue between the staple cartridge and the staple anvil of a stapling apparatus which contains at least one multilayer surgical buttress having a non-porous layer and a porous layer and firing the stapling apparatus to force at least one staple to pass through the openings on the staple cartridge, at least one multilayer buttress, the tissue and the openings on the staple anvil to seal the tissue. Once stapled in place the porous layer advantageously reduces bleeding, assists in sealing the wound and allowing tissue ingrowth, if desired, while the non-porous layer provides support for the porous layer and may assist in preventing the formation of adhesions. In addition, the multilayer buttress may optionally include an additional reinforcement member (which, as described in more detailed below, may be absorbable or non-absorbable) to provide additional support to the multilayer buttress and assist in preventing tears during stapling.

It should be understood that buttresses need not be associated with both the staple cartridge and the anvil. Rather, a buttress may be associated with only the staple cartridge and not the anvil or with the anvil and not the staple cartridge. In addition, the multilayer surgical buttress described herein may be configured into any shape, size or dimension suitable to fit any surgical stapling, fastening or firing apparatus. Other examples of stapling apparatus which may utilize the multilayer buttress material described herein includes laparoscopic staplers (see, e.g., U.S. Pat. Nos. 6,330,965 and 6,241,139, the entire contents of which are incorporated herein by this reference), alternative stapling apparatus of the transverse anastomosis type for stapling a patient's mesentery (see, e.g., U.S. Pat. No. 5,964,394, the entire content of which is incorporated herein by this reference), and end-to-end anastomosis types for performing surgical anastomotic stapling with a circular cartridge and anvil mesentery (see, e.g., U.S. Pat. No. 5,915,616, the entire content of which is incorporated herein by this reference). The present buttresses may also be used in conjunction with instruments that apply two-part fasteners wherein a first part of the two-part fastener is stored in a cartridge or like member and can be fired and properly joined to a second part of the two-part fastener disposed in an anvil or like member. Those skilled in the art having read the present disclosure will readily envision how to adapt the present buttresses for use in connection with such apparatus and also envision other surgical apparatus with which the buttresses described herein may be used.

Figure 3A:
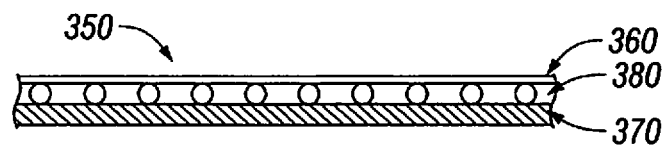
FIG. 3A is a side view of a multilayer buttress as described in one embodiment herein.
Figure 3B:
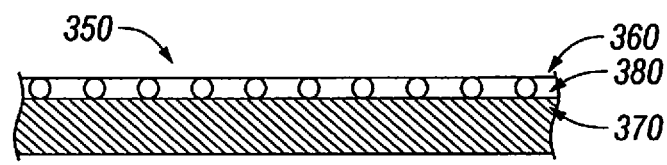
FIG. 3B is a side view of a multilayer buttress as described in one embodiment herein.

Now turning to FIGS. 3A and 3B, buttress 350 is shown having a non-porous layer 360 and a porous layer 370. It is envisioned that buttress 350 may contain a plurality of layers in which any combination of non-porous and porous layers may be configured. For example, a multilayer buttress may be formed in which multiple non-porous layers and porous layers are stacked in an alternating manner. In another example, the multilayer buttress may be formed in a "sandwich-like" manner wherein the outer layers of the multilayer buttress include porous layers and the inner layers are non-porous layers. It is further envisioned that the non-porous layer and porous layer may be positioned in any order relative to the surfaces of staple cartridge and staple anvil.

The non-porous layer of the buttress may be made from any biocompatible material. Thus, the non-porous layer of the multilayer buttress described herein may be formed from a natural material or a synthetic material. The material from which the non-porous layer is formed may be bioabsorbable or non-bioabsorbable. It should of course be understood that any combination of natural, synthetic, bioabsorbable and non-bioabsorbable materials may be used to form the non-porous layer. Some non-limiting examples of materials from which the non-porous layer may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the non-porous layer of the buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce the support layer of the buttress.

In embodiments, collagen of human and/or animal origin, e.g., type I porcine or bovine collagen, type I human collagen or type III human collagen, may be used to form the non-porous layer.

Native collagen may advantageously be used in acid solution or after processing, to eliminate the telopetpides, notably by pepsin digestion. The collagen, e.g., atelocollagen, can also be modified by oxidative cleavage by the use of periodic acid or one of its salts. The oxidative cleavage of the collagen allows for future moderate crosslinking in the collagenic material with other polymeric materials, macromolecular additives or the haemostatic agents contained in the haemostatic layer of the buttress.

In embodiments, the non-porous layer according to the present disclosure is made of collagen which is oxidized or a mixture in any proportions of non-oxidized and oxidized collagens.

In embodiments, at least one macromolecular additive may be combined with the collagen to provide a composition from which the non-porous layer is formed. Some examples of suitable macromolecular additives include, polyethylene glycol, glycerin, polysaccharides, dextran, maltodextrin, mucopolysaccharides, cellulose, alginate and combinations thereof. When used, the macromolecular additive may have a molecular weight of at least 3,000 Daltons and may represent a concentration from about 2 to 10 times less than the collagenic material present in the composition from which the non-porous layer is formed.

The non-porous layer may enhance the ability of the buttress to resist tears and perforations during the manufacturing, shipping, handling and stapling processes. Also, the non-porous layer may also retard or prevent tissue ingrowth from surrounding tissues thereby acting as an adhesion barrier and preventing the formation of unwanted scar tissue. Thus, in embodiments, the non-porous layer possesses anti-adhesion properties.

It is envisioned that the buttress may be releasably attached to the cartridge and/or the anvil in any manner capable of retaining the buttress in contact with the cartridge and/or the anvil prior to and during the stapling process, while allowing the buttress to be removed or released from the cartridge and/or the anvil following the penetration of the buttress by a surgical staple or other fastening device. For example, the buttress may be attached to the cartridge and/or the anvil using adhesives, sealants, glues, pins, tacks, tabs, clamps, channels, straps, protrusions and combinations thereof.

The non-porous layer may be formed using techniques within the purview of those skilled in the art, such as casting, molding and the like.

Figure 5A:
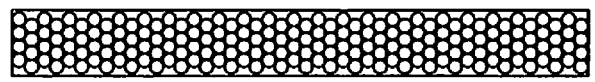
FIG. 5A schematically shows a porous layer wherein the pores or openings extend across the entire thickness thereof in accordance with embodiments of the present disclosure.
Figure 5B:
FIG. 5B schematically shows a porous layer wherein the pores or openings do not extend across the entire thickness thereof in accordance with embodiments of the present disclosure.
Figure 5C:
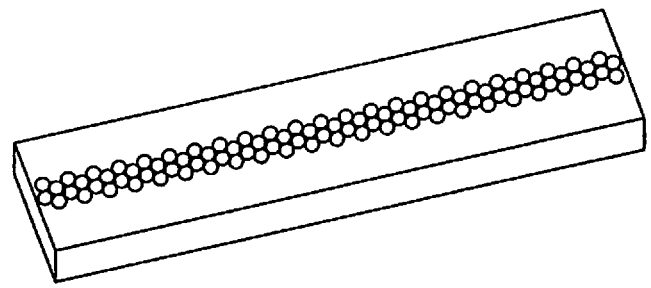
FIG. 5C schematically shows a porous layer wherein the pores or openings are present on only a portion of the surface thereof in accordance with embodiments of the present disclosure.

The porous layer of the buttress has openings or pores over at least a portion of a surface thereof. As described in more detail below, suitable materials for forming the porous layer include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the porous layer. Woven fabrics, kitted fabrics and open cell foam are illustrative examples of structures in which the pores can be in sufficient number and size so as to interconnect across the entire thickness of the porous layer. In embodiments, the pores do not interconnect across the entire thickness of the porous layer. Closed cell foam or fused non-woven materials are illustrative examples of structures in which the pores may not interconnect across the entire thickness of the porous layer. FIG. 5A schematically illustrates a foam porous layer wherein the pores span across the entire thickness of porous layer. In yet other embodiments, the pores do not extend across the entire thickness of the porous layer, but rather are present at a portion of the surface thereof. FIG. 5B schematically illustrates a porous layer wherein the pores do not span across the entire thickness thereof. In embodiments, the openings or pores are located on a portion of the surface of the porous layer, with other portions of the porous layer having a non-porous texture. FIG. 5C schematically illustrates a porous layer wherein the pores do not cover the entire surface of the porous layer, but rather are present on a central portion thereof. Those skilled in the art reading the present disclosure will envision other pore distribution patterns and configurations for the porous layer.

Where the porous layer is fibrous, the fibers may be filaments or threads suitable for knitting or weaving or may be staple fibers, such as those frequently used for preparing non-woven materials. The fibers may be made from any biocompatible material. Thus, the fibers may be formed from a natural material or a synthetic material. The material from which the fibers are formed may be bioabsorbable or non-bioabsorbable. It should of course be understood that any combination of natural, synthetic, bioabsorbable and non-bioabsorbable materials may be used to form the fibers. Some non-limiting examples of materials from which the fibers may be made include, but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

Where the porous layer is fibrous, the porous layer may be formed using any method suitable to forming fibrous structures, including but not limited to knitting, weaving, non-woven techniques and the like. Suitable techniques for making fibrous structures are within the purview of those skilled in the art.

Where the porous layer is a foam, the porous layer may be formed using any method suitable to forming a foam or sponge including, but not limited to the lyophilization or freeze-drying of a composition. Suitable techniques for making foams are within the purview of those skilled in the art.

In embodiments, the porous layer possesses haemostatic properties. Illustrative examples of materials which may be used in providing the porous layer with the capacity to assist in stopping bleeding or hemorrhage include, but are not limited to, poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, epsilon amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof.

Generally, the use of natural biological polymers, and in particular proteins, is particularly useful in forming porous layers having haemostatic properties. Suitable natural biological polymers include, but are not limited to, collagen, gelatin, fibrin, fibrinogen, elastin, keratin, albumin and combinations thereof. In such embodiments, the natural biological polymers may be combined with any other haemostatic agent to produce the porous layer of the buttress. The origin and types of collagens that may be used to form the porous layer are the same as those indicated above for the non-porous layer. However, the oxidized or non-oxidized collagen may be lyophilized, freeze-dried, or emulsified in the presence of a volume of air to create a foam and then freeze-dried, to form a porous compress.

In embodiments, the porous layer may be made from denatured collagen or collagen which has at least partially lost its helical structure through heating or any other method, consisting mainly of non-hydrated α chains, of molecular weight close to 100 kDa. The term "denatured collagen" means collagen which has lost its helical structure. The collagen used for the porous layer as described herein may be native collagen or atellocollagen, notably as obtained through pepsin digestion and/or after moderate heating as defined previously. The collagen may have been previously chemically modified by oxidation, methylation, succinylation, ethylation or any other known process.

In embodiments, the porous layer can be obtained by freeze-drying an aqueous acid solution or suspension of collagen at a concentration of about 2 to about 50 g/l and at an initial temperature of about 4 to about 25° C. The concentration of collagen in the solution can be from about 1 g/l to about 30 g/l and in embodiments about 10 g/l. This solution is advantageously neutralized to a pH of about 6 to about 8.

In embodiments, the porous layer can be at least 0.1 cm thick. In embodiments the thickness of the porous layer can range from about 0.2 to about 1.5 cm thick. The porous layer can have a density of not more than about 75 mg collagen/cm$^2$ and in embodiments below about 7 mg collagen/cm$^2$. The size of the pores in the porous layer can be from about 20 μm to about 200 μm, in embodiments from about 100 μm to about 200 μm.

The haemostatic agents from which the porous layer can be made or which can be included in the porous layer can be in the form of foams, fibers, filaments, meshes, woven and non-woven webs, compresses, pads, powders, flakes, particles and combinations thereof. In embodiments, the porous layer having haemostatic properties provides to the multilayer buttress when hydrated characteristics similar to that of the tissue to which the buttress is applied.

The multilayer buttress material described herein may be formed using any method known to those skilled in the art capable of connecting a non-porous layer to a porous layer. It is envisioned that the non-porous layer and the porous layer may be adhered to one another using chemical bonding, surgical adhesives, surgical sealants, and surgical glues. In addition, the layers may be bound together using mechanic means such as pins, rods, screws, clips, etc. Still further, the layers may naturally or through chemical or photoinitiation may interact and crosslink or provide covalent bonding between the layers.

In embodiments, the multilayer buttress described herein is prepared by attaching the individual layers of materials together to form a multiple layer buttress. The porous layer may be formed separate and apart from the non-porous layer. Alternatively, the porous and non-porous layers may be formed together.

In some embodiments, the porous layer may be attached to the non-porous layer, in a manner which allows the two layers to crosslink and form a chemical bond creating a multilayer buttress material capable of sealing tissue. One such example includes pouring a solution of the material from which the non-porous layer is to be made into a mold and applying the porous layer to the poured solution during the gelification process. As described in U.S. Pat. No. 6,596,304, which the entire content of which is incorporated herein by reference, the porous layer may contain a porous compress made from collagen. The non-porous layer may be made from a biopolymer film containing collagen, polyethylene and glycerol. The porous layer may be added to the non-porous film and allowed to crosslink to form multilayer material suitable for reinforcing a staple or suture line.

As further shown in FIGS. 3A and 3B, buttress 350 may also include a reinforcement member 380. In FIG. 3A, reinforcement member 380 is shown being positioned between non-porous layer 360 and porous layer 370 of buttress 350 and in FIG. 3B, reinforcement member 380 is shown being positioned solely within an individual layer, supporting in this case non-porous layer 360 of buttress 350. It is envisioned that reinforcement member 380 may also be positioned within the porous layer. The reinforcement member may also be positioned at the surface of one of the layers making up the multilayer buttress and, in embodiments, may be positioned at an exterior surface of the multilayer buttress.

Figure 3C:
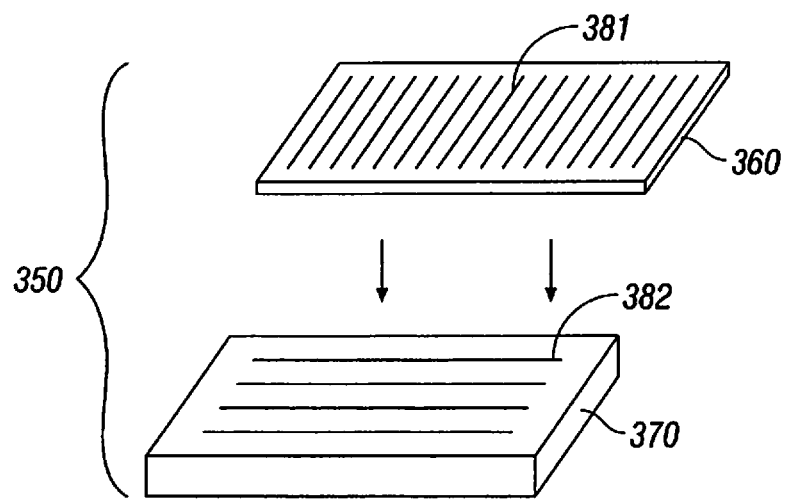
FIG. 3C shows an illustrative embodiment wherein fibers present in more than one layer are used as the reinforcement member, with the fibers in one layer being oriented in a first common direction and the fibers in the other layer being oriented in a second common direction that is substantially perpendicular to the first common direction.
Figure 3D:
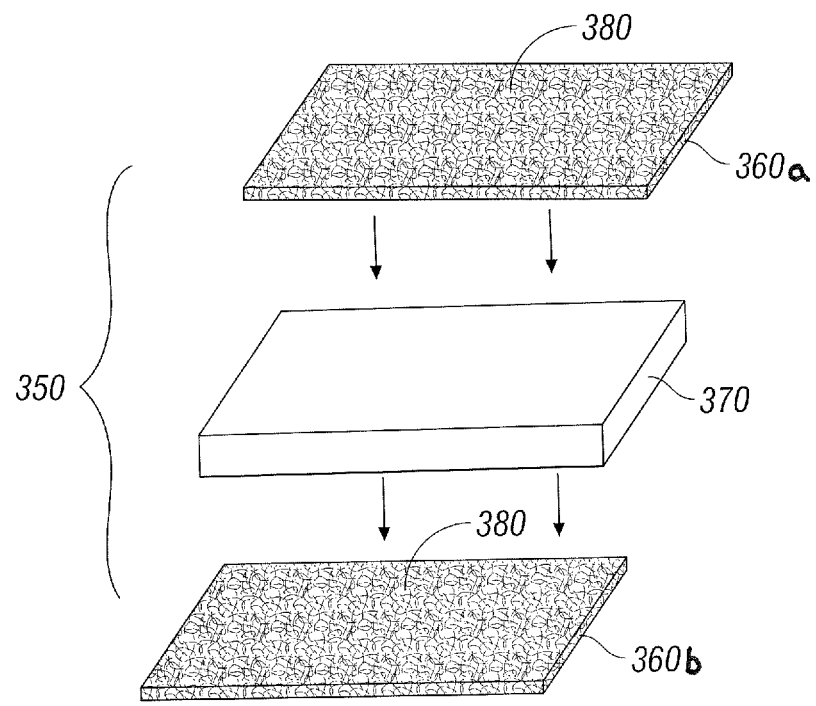
FIG. 3D shows an illustrative embodiment wherein chopped fibers are used as the reinforcement member.

Some suitable non-limiting examples of the reinforcement member include meshes, monofilaments, multifilament braids, chopped fibers (sometimes referred to in the art as staple fibers) and combinations thereof.

Where the reinforcement member is a mesh, it may be prepared using any technique known to those skilled in the art, such as knitting, weaving, tatting, knipling or the like.

Where monofilaments or multifilament braids are used as the reinforcement member, the monofilaments or multifilament braids may be oriented in any desired manner. For example, the monofilaments or multifilament braids may be randomly positioned with respect to each other within the buttress structure. As another example, the monofilaments or multifilament braids may be oriented in a common direction within the buttress. In embodiments, monofilaments or multifilament braids are associated with both the porous layer and with the non-porous layer. In an illustrative embodiment of this type shown in FIG. 3C, buttress 350 includes a first reinforcement member 381 having a plurality of reinforcement members oriented in a first direction within the non-porous layer 360 and a second reinforcement layer 382 having a plurality of reinforcement members oriented in a second direction within the porous layer 370. In embodiments, the first and second directions may be substantially perpendicular to each other as seen in FIG. 3C.

Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped fibers may be from 0.1 mm to 100 mm in length, in embodiments, 0.4 mm to 50 mm in length. FIG. 3D shows an illustrative embodiment wherein buttress 350 has chopped fibers 380 incorporated in first non-porous layer 360a and in second non-porous layer 360b which can be applied to opposing sides of porous layer 370.

It is envisioned that the reinforcement member may be formed from any bioabsorbable, non-bioabsorbable, natural, and synthetic material previously described herein including derivatives, salts and combinations thereof. In particularly useful embodiments, the reinforcement member may be made from a non-bioabsorbable material to provide long term flexible tissue support. In embodiments, the reinforcement member is a surgical mesh made from polypropylene or polylactic acid. In addition polyethylene materials may also be incorporated into the buttress described herein to add stiffness. Where monofilaments or multifilament braids are used as the reinforcement member, any commercially available suture material may advantageously be employed as the reinforcement member.

Figure 4:
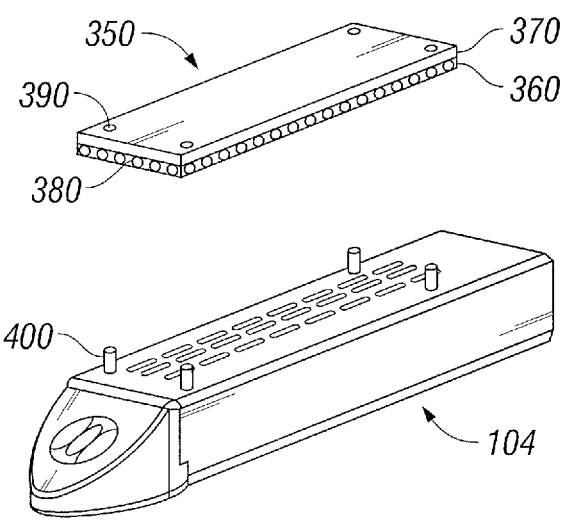
FIG. 4 is a perspective view of a staple cartridge that includes a multilayer buttress releasably attached thereto.

Turning now to FIG. 4, one embodiment is shown in which multilayer buttress 350 includes at least one hole 390 which is shaped and designed to frictionally fit onto at least one pin 400 located on staple cartridge 104 and/or staple anvil 204. Hole 390 and pin 400 are designed to releasably attach multilayer buttress 350 to staple cartridge 104 and/or staple anvil 204 and both can be of any size, shape or dimension.

In some embodiments, at least one bioactive agent may be combined with the buttress material and/or any of the individual components (the porous layer, the non-porous layer and/or the reinforcement member) used to construct the buttress material. In these embodiments, the buttress material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the medial device in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the bioactive coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin, lactoferricin B and antimicrobial polysaccharides such as fucans and derivatives may be included as a bioactive agent in the bioactive coating of the present disclosure.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

EXAMPLE 1

Preparation of Porous Layer

Type I porcine collagen is extracted from pig dermis and rendered soluble through pepsin digestion and purified by saline precipitation.

A 10 g/l solution of the collagen is prepared by dissolving 23 g of damp collagen (12% humidity) in 2070 g of ultrafiltered water, at an ambient temperature below 25° C. It is neutralized using sodium hydroxide to a neutral pH, which leads to precipitation of the collagen.

A porous layer suitable for use in making a multilayer buttress is prepared by poring the suspension onto freeze-dry plates, with 0.5 to 1 g/cm² and freeze-drying, using one cycle lasting about 24 hours.

Optionally, in a variant, the freeze-dried porous layer so produced can be heated to 60° C. for several hours (4 to 15), which provides it with better cohesion and mechanical resistance in certain applications.

Preparation of a Solution of Oxidized Collagen Used to Form a Non-Porous Film

Type I porcine collagen is extracted from pig dermis and rendered soluble through pepsin digestion and purified by saline precipitation.

A 30 g/l solution of oxidized collagen used for this example, is prepared according to patent FR-A-2 715 309.

Dry collagen fibres are used for preference, obtained by precipitation of an acid solution of collagen by adding NaCl, then washing and drying the precipitate obtained using aqueous solutions of acetone in concentrations increasing from 80% to 100%.

A 30 g/l solution of collagen is prepared by dissolving it in 0.01 N HCl. Its volume is 49 liters. Periodic acid is added to it at a final concentration of 8 mM, i.e. 1.83 g/l. Oxidation takes place at an ambient temperature close to 22° C. for 3 hours away from light.

Then an equal volume of a solution of sodium chloride is added to the solution to obtain a final concentration of 41 g/l NaCl.

After waiting for 30 minutes, the precipitate is collected by decantation through a fabric filter, with a porosity close to 100 microns, then washed 4 times with a 41 g/l solution of NaCl in 0.01 N HCl. This produces 19 kg of acid saline precipitate. This washing process eliminates all traces of periodic acid or iodine derivatives during oxidation of the collagen.

Then, several washes in an aqueous solution of 80% acetone are used to concentrate the collagen precipitate and eliminate the salts present.

A final wash in 100% acetone is used to prepare 3.6 kg of a very dense acetone precipitate of acid, oxidized, non-reticulated collagen, with no trace of undesirable chemical products.

The acetone paste is diluted with apyrogenic distilled water at 40° C., to obtain a 3% concentration of collagen, for a volume of 44 liters. The collagen suspension of a volume of 44 liters is heated for 30 minutes at 50° C., then filtered under sterile conditions through a membrane of 0.45 micron porosity in a drying oven at 40° C.

As soon as this solution is homogeneous and at 35° C., a sterile concentrated solution of PEG 4000 (polyethylene glycol with a molecular weight of 4000 Daltons) and glycerine is added to it to produce a final concentration of 0.9% PEG, 0.54% glycerine and 2.7% oxidized collagen.

As soon as these additions have been made, the pH of the solution is adjusted to 7.0 by adding a concentrated solution of sodium hydroxide.

Preparation of a Multilayer Buttress Material

The collagen solution destined to form the non-porous layer, as described in above, is poured in a thin layer on a flat hydrophobic support such as PVC or polystyrene, at an ambient temperature close to 22° C. A continuous pocket, or channel, or a plurality of longitudinally spaced pockets, or channels, are machined into the surface of the hydrophobic support. The pockets, or channels, in the support correspond to slots or openings in the anvil and/or staple cartridge. The number, dimension and spacial relationship of the pockets, or channels, are determined so as to provide a molded buttress which in turn provides a releasable pressure fit with the slots or openings provided in the anvil or staple cartridge when placed in cooperation therewith.

The porous layer, prepared as described above, is applied uniformly to the solution of heated collagen, 5 to 20 minutes after it was poured onto the support. This waiting time is the collagen solution gelling time, required for application of the porous layer, to prevent it dissolving or becoming partially hydrated in the liquid collagen.

Penetration of the porous layer into the gelled collagen solution can be less than 0.5 mm.

The buttress material is then dehydrated in a jet of sterile air, at ambient temperature, which leads to evaporation in about 18 hours.

The multilayer buttress material obtained is easy to remove from the support and can be cut to the dimensions required for the application concerned, without weakening it.

The multilayer buttress material is then put into an airtight double polyethylene bag.

The unit is sterilized by gamma irradiation or electron beam (beta) irradiation at a dose of between 25 and 35 KGy.

EXAMPLE 2

Preparation of a Multilayer Buttress Material

The collagen solution destined to form the non-porous layer, as described above in EXAMPLE 1, is poured in a thin layer equal to about 0.106 g/cm² on a flat hydrophobic support such as PVC or polystyrene, at an ambient temperature close to 22° C. Several protrusions are machined onto the surface of the mold. The protrusions on the mold correspond to the pins located on the anvil and/or staple cartridge. The number, dimension and special relationship of the protrusions, are determined so as to provide a molded buttress which in turn provides a releasable pressure fit with the pins provided on the anvil or staple cartridge when placed in cooperation therewith.

The remaining collagen solution is diluted with ethyl alcohol and water to produce a final concentration of 1.75% of oxidized collagen.

Using the diluted solution of 1.75% oxidized collagen, a second layer equal to about 0.041 g/cm² is poured over the first layer, 1 hour or more after the spreading of the first layer.

Immediately, a surgical mesh reinforcement member is applied on the second layer of the diluted oxidized collagen. The reinforcement member is a knitted isoelastic, multifilament polyglycolic acid mesh which may be completely encapsulated by the second layer of oxidized collagen.

After 1 hour or more, the porous layer, prepared as described above in EXAMPLE 1, is applied to the mesh.

The multilayer, reinforced buttress material is dried in a drying cabinet at about 20° C. and about 40% humidity with a horizontal air flow velocity of 1.2 m²/s. The air is blown from the right side of the cabinet to the left side of the cabinet and the incoming air is 0.2 μm filtered and adjusted to 40% humidity. The duration of the drying cycle is between 12 and 24 hours.

EXAMPLE 3

Preparation of a Multilayer Buttress Material

The collagen solution destined to form the non-porous, as described above in EXAMPLE 1, is poured in a thin layer equal to about 0.106 g/cm² on a flat hydrophobic support such as PVC or polystyrene, at an ambient temperature close to 22° C. The remaining collagen solution is diluted with ethyl alcohol and water to produce a final concentration of 1.75% of oxidized collagen.

Using the diluted solution of 1.75% oxidized collagen, a second layer equal to about 0.041 g/cm² is poured over the first layer, 1 hour or more after the spreading of the first layer.

Immediately, a surgical mesh reinforcement member, is applied on the second layer of the diluted oxidized collagen. The reinforcement member is a knitted isoelastic, multifilament polyglycolic acid mesh which may be positioned on top of the second layer of oxidized collagen.

After 1 hour or more, the porous layer, prepared as described above in EXAMPLE 1, is applied to the mesh.

The multilayer, reinforced buttress material is dried in a drying cabinet at about 20° C. and about 40% humidity with a horizontal air flow velocity of 1.2 m²/s. The air is blown from the right side of the cabinet to the left side of the cabinet and the incoming air is 0.2 μm filtered and adjusted to 40% humidity. The duration of the drying cycle is between 12 and 24 hours.

The multilayer buttress of EXAMPLES 1-3 are applied to the staple cartridge and/or anvil of a surgical stapler, with the non-porous side in contact with the surface of the cartridge and/or anvil. The edges of a wound are approximated between the staple cartridge and the staple anvil of the stapling apparatus. By firing the stapling apparatus staples are forced out of the staple cartridge and through both the multilayer buttress and, the tissue. The staples are formed by contact with the staple anvil. Once stapled in place the porous layer advantageously reduces bleeding, assists in sealing the wound and allowing tissue ingrowth, if desired, while the non-porous layer provides support for the porous layer and may assist in preventing the formation of adhesions. When present, as in EXAMPLES 2 and 3, the reinforcement member provides additional support to the multilayer buttress and assist in preventing tears during stapling.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A surgical stapling apparatus comprising:
    a staple cartridge containing at least one staple;
    an anvil having a staple forming surface; and
    a buttress positioned adjacent the anvil or the cartridge, the buttress comprising a non-porous layer disposed between first and second porous layers and a reinforcement member positioned within the non-porous layer,
    wherein pores of the porous layers do not span across the entire thickness of the porous layers.

2. The surgical stapling apparatus of claim 1, wherein the non-porous layer comprises at least one material selected from the group consisting of collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethylcellulose, chitan, chitosan, alginate, poly(lactic acid), poly(glycolic acid), poly(hydroxybutyrate), poly (phosphazine), polyesters, polyethylene glycols, polyalkyleneoxides, polyacrylamides, polyhydroxyethylmethylacrylate, polyvinylpyrrolidone, polyvinyl alcohols, poly(caprolactone), poly(dioxanone), polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and combinations thereof.

3. The surgical stapling apparatus of claim 1, wherein the porous layer comprises at least one material selected from the group consisting of poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, epsilon amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof.

4. The surgical stapling apparatus of claim 1, wherein the reinforcement member is a mesh.

5. The surgical stapling apparatus of claim 1, wherein the reinforcement member is a suture.

6. The surgical stapling apparatus of claim 1, comprising a plurality of reinforcement members oriented in at least one common direction.

7. The surgical stapling apparatus of claim 1, wherein the reinforcement member is encapsulated within the non-porous layer.

8. The surgical stapling apparatus of claim 1, wherein a first reinforcement member is encapsulated within the non-porous layer and a second reinforcement layer is encapsulated within the porous layer.

9. The surgical stapling apparatus of claim 8, wherein the first reinforcement member comprises a plurality of reinforcement members oriented in a first direction within the non-porous layer and the second reinforcement layer comprises a plurality of reinforcement members oriented in a second direction within the porous layer.

10. The surgical stapling apparatus of claim 1, wherein the pores of the porous layer are present on a central portion thereof.

11. The surgical stapling apparatus of claim 1, wherein the buttress further comprises a bioactive agent.

12. The surgical stapling apparatus of claim 11, wherein the bioactive agent is combined with the porous layer.

13. The surgical stapling apparatus of claim 11, wherein the bioactive agent is combined with the non-porous layer.

14. The surgical stapling apparatus of claim 11, wherein the bioactive agent is combined with the reinforcement member.

15. A surgical stapling apparatus comprising:
a staple cartridge containing at least one staple;
an anvil having a staple forming surface; and
a buttress positioned adjacent the anvil or the cartridge, the buttress comprising a non-porous layer disposed between first and second porous layers, and a reinforcement member positioned within the non-porous layer,
wherein the reinforcement member comprises chopped fibers and wherein pores of the porous layers do not span across the entire thickness of the porous layers.

16. A method of sealing a wound comprising:
enclosing tissue between a cartridge and an anvil of a surgical stapling apparatus, one of the cartridge or anvil having a buttress positioned adjacent thereto, the buttress comprising a non-porous layer disposed between first and second porous layers having pores which do not span across the entire thickness of the porous layers, and a reinforcement member positioned within the non-porous layer; and
ejecting staples from said cartridge to secure the buttress to the tissue.

* * * * *